United States Patent
Nishi et al.

(10) Patent No.: US 8,435,782 B2
(45) Date of Patent: May 7, 2013

(54) CELL CULTURE CONTAINER AND METHOD OF PRODUCING THE SAME

(75) Inventors: Taiji Nishi, Kurashiki (JP); Go Tazaki, Tsukuba (JP); Motohiro Fukuda, Tsukuba (JP); Michio Yazawa, Sapporo (JP); Masayuki Takahashi, Sapporo (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 419 days.

(21) Appl. No.: 12/280,607

(22) PCT Filed: Feb. 19, 2007

(86) PCT No.: PCT/JP2007/052972
§ 371 (c)(1),
(2), (4) Date: Aug. 25, 2008

(87) PCT Pub. No.: WO2007/105418
PCT Pub. Date: Sep. 20, 2007

(65) Prior Publication Data
US 2009/0170190 A1    Jul. 2, 2009

(30) Foreign Application Priority Data
Feb. 24, 2006   (JP) .................................. 2006-048045

(51) Int. Cl.
*C12M 1/14* (2006.01)
(52) U.S. Cl.
USPC ...................................................... 435/299.1

(58) Field of Classification Search ............... 435/299.1;
C12M 1/22, 25/06, 27/14, 23/10, 23/12;
B01D 53/84, 53/85; B01L 13/5085
See application file for complete search history.

(56) References Cited

U.S. PATENT DOCUMENTS

| | | | |
|---|---|---|---|
| 2003/0148401 A1* | 8/2003 | Agrawal et al. | 435/7.9 |
| 2005/0034200 A1* | 2/2005 | Montemagno et al. | 427/2.28 |
| 2005/0214935 A1 | 9/2005 | Kuwabara et al. | |
| 2006/0281172 A1* | 12/2006 | Kuwabara et al. | 435/305.2 |

FOREIGN PATENT DOCUMENTS

| | | |
|---|---|---|
| JP | 56 9906 | 1/1981 |
| JP | 63 196281 | 8/1988 |
| JP | 1 141588 | 6/1989 |

(Continued)

OTHER PUBLICATIONS

U.S. Appl. No. 12/665,474, filed Dec. 18, 2009, Tazaki, et al.

(Continued)

*Primary Examiner* — Michael Hobbs
(74) *Attorney, Agent, or Firm* — Oblon, Spivak, McClelland, Maier & Neustadt, L.L.P.

(57) ABSTRACT

An object of the present invention is to provide a cell culture chamber with which the survival rate of cells to be cultured can be increased, and a method of producing the same. A cell culture chamber according to the present invention includes a mass of projections formed of a plurality of microprojections 1 formed on a surface on which cells are cultured. The width or diameter of each of the microprojections 1 is in a range of 20 nm to 3 µm, and the aspect ratio of each of the microprojections is in a range of 0.2 to 3.0. Thus, there can be provided a cell culture chamber most suitable for the adhesion and differentiation/proliferation of cells to be cultured.

8 Claims, 6 Drawing Sheets

FOREIGN PATENT DOCUMENTS

| | | |
|---|---|---|
| JP | 5 230249 | 9/1993 |
| JP | 7 23768 | 1/1995 |
| JP | 8 116963 | 5/1996 |
| JP | 2004/154027 | 6/2004 |
| JP | 2005 80607 | 3/2005 |
| JP | 2005 168494 | 6/2005 |
| JP | 2005 312343 | 11/2005 |
| JP | 2005 328727 | 12/2005 |
| JP | 2006 191809 | 7/2006 |
| WO | 2006 123570 | 11/2006 |
| WO | 2007 032208 | 3/2007 |
| WO | 2007/049576 | 5/2007 |

OTHER PUBLICATIONS

Lampin, M. et al., "Correlation Between Substratum Roughness and Wettability, Cell Adhesion, and Cell Migration", Journal of Biomedical Materials Research, vol. 36, No. 1, pp. 99-108 (1997).

U.S. Appl. No. 13/229,087, filed Sep. 9, 2011, Tazaki, et al.

Extended European Search Report issued May 7, 2012 in patent application No. 07714498.8.

Office Action dated Jan. 8, 2013 as received in the corresponding Japanese Patent Application No. 2008-505014 (English Translation Only).

\* cited by examiner

CELL CULTURE CONTAINER AND METHOD OF PRODUCING THE SAME

CROSS-REFERENCE TO RELATED APPLICATIONS

This application is a 371 of PCT/JP07/52972 filed Feb. 19, 2007 and claims the benefit of JP 2006 048045 filed Feb. 24, 2006.

TECHNICAL FIELD

The present invention relates to a cell culture chamber and a method of producing the same.

BACKGROUND ART

Cell death is roughly classified into apoptosis and necrosis. Apoptosis is a form of death of cells constituting a body of a multicellular organism. Apoptosis refers to controlled and regulated cellular suicide which is actively caused to keep an individual in better condition. On the other hand, necrosis refers to cell death caused by a deterioration of environment inside and outside cells due to an external injury, poor blood circulation, or the like.

Necrosis refers to local death of living tissue.

Unlike normal death, in necrosis, only cells constituting a part of a body become extinct. The causes of necrosis include infection, physical disruption, chemical injury, and a reduction in blood flow. Necrosis due to a reduction in blood flow is particularly called infarction. Even when cells are dead, if normal cells and tissue, such as blood cells, skin, and mucosal epithelium of digestive tract, are continually replenished without leaving a functional disorder or histological abnormality, such cell death is not called necrosis. The dead tissue is finally removed by an immune system of an organism, and a defective part is compensated by regeneration or fibrosis of the original tissue.

For testing and studying the cells, it is necessary to culture cells isolated from tissue. In recent years, the cell culture is carried out for a variety of purposes such as drug discovery/development, production of drugs, basic tests in regenerative medicine, and evaluation of drugs. The cell culture is indispensable in fields related to biotechnology. The research and development speed depends on the adhesion ability of cells to be cultured in a cell incubator, since the adhesion ability is an extremely important factor for the differentiation/proliferation ability of the cells. Further, cell lines to be used for the culture test are extremely expensive, which affects test cost directly.

It is known that, in the case of culturing cells in a cell culture chamber such as a petri dish made of plastic, a petri dish made of glass, a glass plate fixed into the chamber, or a well plate, a pH change due to carbon dioxide gas exhausted from cultured cells largely affects the activity of the cultured cells. In the conventional long-time culture, culture solution is periodically replaced by a worker, thereby keeping the activity of the cultured cells.

Further, Patent Document 1 proposes a cell culture chamber characterized by including a mass of projections each having an equivalent diameter of 10 nm to 1 mm formed on the surface of the cell culture chamber. Through the formation of a mass of projections, culture solution is allowed to spread over a lower part of the cells to promote the supply of nutritive substances necessary for the cells and the elimination of waste products discharged from the cells. In addition, the cells are brought into contact with the chamber by point contact, thereby preventing the cells from being damaged when the cells are removed.

[Patent Document 1] Japanese Unexamined Patent Application Publication No. 2005-168494

DISCLOSURE OF THE INVENTION

Problem to be Solved by the Invention

However, to suppress necrosis of tissues which are not regenerated, such as nerve cells, cardiac muscle, skeletal muscle, and to suppress the death of cells of tissues which are usually difficult to be cultured, such as nerve cells, cardiac muscle, and liver cells, the replacement of the culture solution with fresh one is insufficient to achieve suppression of the cell death at present. In particular, cultural species that are usually difficult to be cultured have a survival rate of about 20 to 40% with respect to the number of cells initially placed, even if the culture solution is replaced with fresh one.

Further, according to the method disclosed in Patent Document 1, through the formation of a mass of projections, the culture solution is allowed to spread over the lower part of the cells, thereby making it possible to promote the supply of nutritive substances necessary for the cells and the elimination of waste products discharged from the cells. However, since the cells are brought into contact with the chamber by point contact, there arises a problem in that pseudo-scaffolding serving as a desmosome cannot be formed on the surface of a substrate, thereby making it impossible for the cells to sufficiently differentiate and proliferate.

The present invention has been made to solve the above-mentioned problem, and it is an object of the present invention to provide a cell culture chamber with which the survival rate of cells to be cultured can be increased, and a method of producing the same.

Means for Solving the Problem

A cell culture chamber according to the present invention includes a mass of projections formed of a plurality of microprojections on a surface on which cells are cultured, in which a width or diameter of each of the microprojections is in a range of 20 nm to 3 μm, and an aspect ratio of each of the microprojections is in a range of 0.2 to 3.0.

A method of producing a cell culture chamber according to the present invention includes the steps of: forming a pattern above a substrate; forming a metal structure by depositing a metal in accordance with the pattern formed above the substrate or a transcription pattern thereof; forming a cell culture chamber by transcribing a pattern of the metal structure; and forming a mass of projections formed of a plurality of microprojections on a surface on which cells of the cell culture chamber are cultured.

ADVANTAGEOUS EFFECTS OF THE INVENTION

According to the present invention, it is possible to provide a cell culture chamber with which the survival rate of cells to be cultured can be increased, and a method of producing the same.

Description of Reference Numerals

| | |
|---|---|
| 1 | MICROPROJECTION |
| 2 | RECESS |
| 3 | FIRST PROTRUSION |
| 4 | SECOND PROTRUSION |
| 5 | TWO-STAGE PROTRUSION |
| 6 | SIDE WALL OF FIRST PROTRUSION |
| 7 | SIDE WALL OF SECOND PROTRUSION |
| 11 | SUBSTRATE |
| 12 | FIRST RESIST LAYER |
| 13 | MASK A |
| 14 | SECOND RESIST LAYER |
| 15 | MASK B |
| 16 | RESIST PATTERN |
| 17 | CONDUCTIVE FILM |
| 18 | METAL STRUCTURE |
| 19 | RESIN MOLDED PRODUCT |

BEST MODES FOR CARRYING OUT THE INVENTION

As a result of an intensive study, the inventors of the present invention have found it possible to provide a cell culture chamber most suitable for the adhesion and differentiation/proliferation of cultured cells, by setting the dimensions and aspect ratio of microprojections formed on the surface of a cell culture chamber such as a plate or a petri dish, within a desired range. Cells are cultured on the surface of the cell culture chamber. Hereinafter, embodiments of the present invention are described with reference to the drawings.

Embodiment 1

Figure 1A:
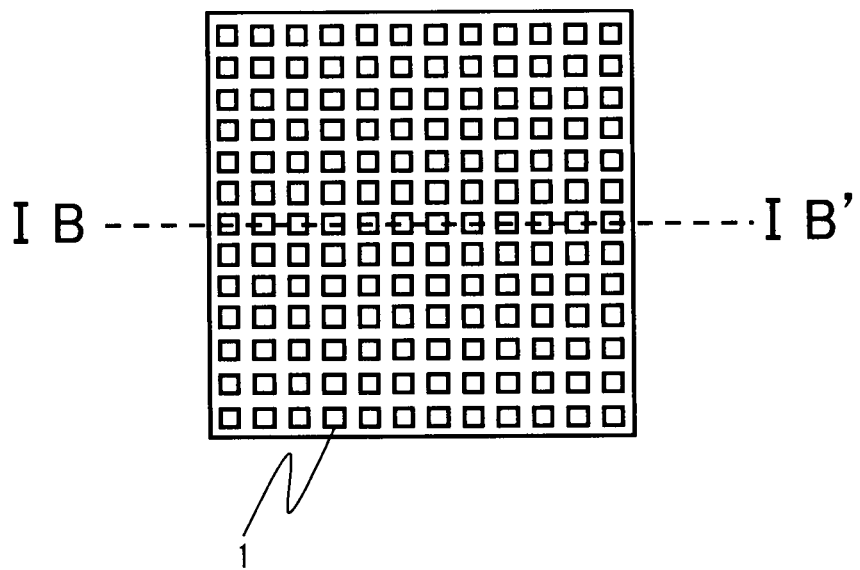
FIG. 1A is a diagram schematically showing the structure of a cell culture chamber according to Embodiment 1 of the present invention.
Figure 1B:
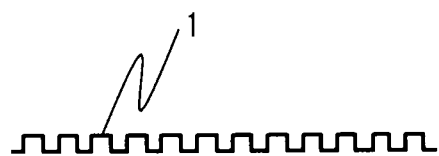
FIG. 1B is a diagram schematically showing the structure of the cell culture chamber according to Embodiment 1 of the present invention.

FIG. 1A is a plan view showing the structure of a cell culture chamber according to Embodiment 1 of the present invention. FIG. 1B is a cross-sectional view taken along the line IB-IB' of FIG. 1A. The cell culture chamber according to Embodiment 1 includes microprojections 1 formed on the surface on which cells are cultured. Note that the microprojections 1 shown in FIGS. 1A and 1B each have a quadrangular prism shape, but may have a columnar shape or a polygonal columnar shape.

The width or diameter of each of the microprojections 1 formed on the surface on which cells are cultured is preferably 20 nm to 3 μm, and more preferably, 100 nm to 1.5 μm. If the width or diameter of each of the microprojections 1 is smaller than 20 nm, it is difficult for cells having a diameter of about 3 μm to 20 μm to recognize the microprojections 1. As a result, it becomes difficult to form a desmosome serving as pseudo-scaffolding, which results in a reduction in differentiation/proliferation rate of cells. On the contrary, if the width or diameter of each of the microprojections 1 is larger than 3 μm, it becomes difficult to form pseudo-scaffolding since the width or diameter approaches the diameter of each cell, which results in a reduction in adhesion ability of the cells. The aspect ratio of the microprojections 1 is preferably in a range of 0.2 to 3.0, and more preferably, in a range of 0.5 to 2.0 to form a desmosome serving as pseudo-scaffolding and to enable easy industrial reproduction.

The aspect ratio refers to a ratio between the width or diameter and the height of each of the microprojections 1 formed on the surface on which cells are cultured. For example, when the diameter of each of the microprojections 1 is 3 μm and the height thereof is 9 μm, the aspect ratio is 3.0.

A description is given of a method of forming the microprojections 1. The following method is a typical example, and the present invention is not limited thereto. Etching by argon plasma or the like using a vacuum system enables formation of the microprojections 1 each having a width or diameter of about 30 nm. Vacuum evaporation enables formation of an inorganic material including the microprojections 1 each having a width or diameter of about 30 nm to 400 nm, by adjusting a degree of vacuum, distance between a raw material and a substrate. Methods of forming the microprojections 1 each having a width or diameter of 400 nm to 3 μm include sandblasting, dry ice cleaning, laser ablation, organic/inorganic particle coating, electric plating, electroless plating, and deposition of an inorganic material by Kanigen plating.

The microprojections 1 can also be formed by using nano-order patterns, that is, nanopatterns. In a method of forming nanopatterns, nanopatterns are first formed on a photosensitive resin or a silicon substrate by electron beam lithography, X-ray exposure, reduction exposure, or the like. Next, a metal mold is produced by electric plating, and a nanopatterned plate is produced by nanoimprint molding. In those production methods, when the aspect ratio of the microprojections 1 exceeds 3.0, it is necessary to provide a metal mold with precise dimensions. However, facilities and exposure masks for forming nanopatterns are expensive, which raises a problem in that costs for producing the nanopatterned plate increase. As a result of an intensive study, the inventors of the present invention have found that the aspect ratio of each of the microprojections 1 suitable for the adhesion and differentiation/proliferation of cells is in the range of 0.2 to 3.0. As a result, low cost can be achieved.

In the case of observing cells to be cultured, transmitted light observation using an inverted microscope is mainly employed. Accordingly, the dimensions and aspect ratio of the microprojections 1 formed on the surface on which cells are cultured are required to prevent visible light with a wavelength of 450 nm to 600 nm from being scattered, that is, required to obtain transparency. To achieve the adhesion ability, differentiation/proliferation ability, and transparency of the cells, the width or diameter of each of the microprojections 1 is preferably set in a range of 20 nm to 400 nm and the aspect ratio thereof is preferably set in a range of 0.2 to 1.0, and more preferably, the width or diameter of each of the microprojections 1 is set in a range of 100 nm to 300 nm and the aspect ratio thereof is set in a range of 0.5 to 1.0.

In order to set the light transmittance of a resin plate to be equal to that of a glass plate to thereby enable the transmitted light observation, the light transmittance at a wavelength in a range of 300 nm to 800 nm including an ultraviolet range is preferably set to be equal to or greater than 80%, and the haze value is preferably set within 10%. To satisfy the above requirements, it is necessary to use, for the cell culture chamber, an acrylic resin excluding an ultraviolet absorber, or to select materials not having a ring system in the chemical structure, such as polycarbonate (PC) and polystyrene. Furthermore, it is necessary that additives such as antioxidant, viscosity increasing agent, heat-resistant stabilizer, and agglutination-inhibiting agent do not include the ultraviolet absorber.

In fluorescence observation, if light (excitation light) for exciting fluorescent dye is not transmitted through the cell culture chamber, fluorescence (fluorescent radiation light) generated by excitation light cannot be identified. Accordingly, the cell culture chamber is required to have high optical transparency. To obtain the transparency required for identifying the fluorescence (fluorescent radiation light), a whole light transmittance of 80% or higher and a haze value of 10% or smaller with respect to the visible light are necessary. To satisfy the above requirements, it is preferable to use a material excellent in optical property, for example, polymethylmethacrylate for the cell culture chamber. In the case of using a polyolefin resin which is a crystalline resin, it is preferable to use the polyolefin-based resin in an amorphous state.

Self-fluorescence refers to a phenomenon in which polymer molecules emit fluorescence by itself by emitting light after absorbing ultraviolet/visible light. A glass plate does not emit fluorescence by itself, while many of resin plates emit fluorescence by itself. Accordingly, the fluorescence (fluorescent radiation light) generated from a sample cannot be identified, which makes it difficult to perform microanalysis which is a feature of fluorescence analysis.

To eliminate the effect of the self-fluorescence, it is necessary to avoid the self-fluorescence by applying light with a wavelength of 230 nm to 800 nm. Thus, it is necessary to select resin materials not having the ring system in the chemical structure, such as polycarbonate (PC) and polystyrene, for a cell culture chamber. Further, to reduce the possibility of the self-fluorescence as much as possible, it is preferable to use a minimum amount of additives such as antioxidant, viscosity increasing agent, heat-resistant stabilizer, and agglutination-inhibiting agent, or it is preferable not to add such additives.

To perform observation using a polarization microscope or a differential interference microscope without reducing the contrast in differential interference observation, materials having less optical strain are required. Accordingly, it is necessary to select, for the cell culture chamber, materials not having the ring system in the chemical structure, such as polycarbonate (PC) and polystyrene.

When the cell culture chamber is coated with an organic film or an inorganic film, the cell culture chamber can be made hydrophilic or hydrophobic. As a result, it is possible to prevent foam from being adhered to the microprojections and to control the adhesion degree of cells. For example, a method using low-temperature plasma treatment, corona discharge treatment, violet irradiation, or the like, and a method of applying collagen which is protein promoting the adhesion of cells can be employed. Further, a part of the cell culture chamber is covered with a mask, thereby making it possible to coat only the other part thereof with an organic film or an inorganic film. As a result, it is possible to expand the range of culture test conditions.

Embodiment 2

Figure 2A:
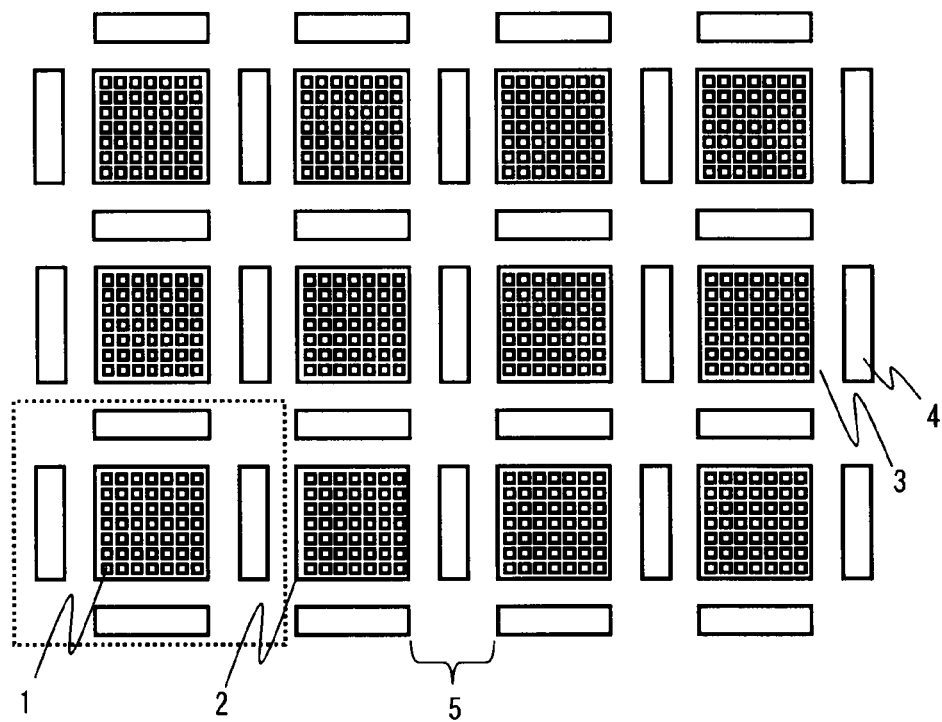
FIG. 2A is a diagram schematically showing the structure of a cell culture chamber according to Embodiment 2 of the present invention.
Figure 2B:
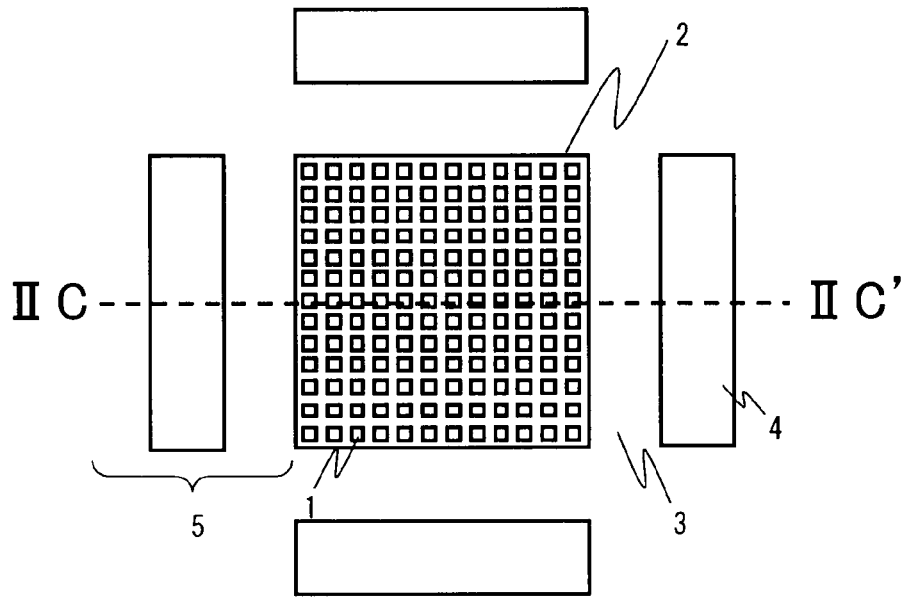
FIG. 2B is a diagram schematically showing the structure of the cell culture chamber according to Embodiment 2 of the present invention.
Figure 2C:
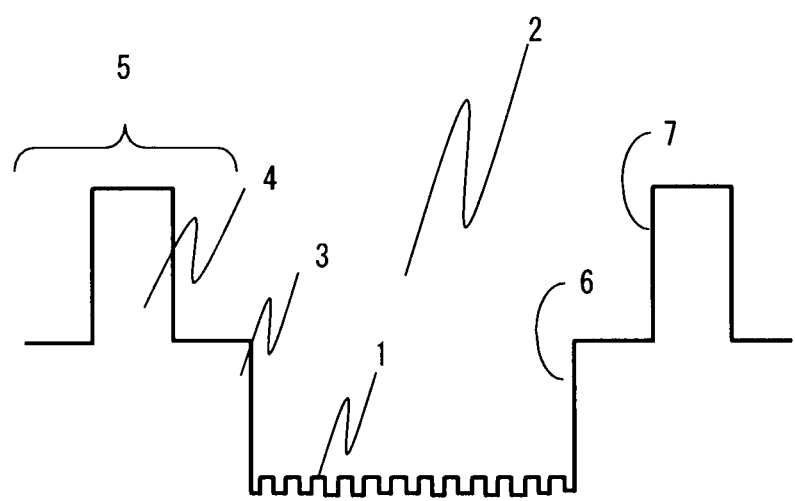
FIG. 2C is a diagram schematically showing the structure of the cell culture chamber according to Embodiment 2 of the present invention.

It is also possible to use a cell culture chamber which includes a plurality of micro-space structures formed on the surface on which cells are cultured, and which is made of resin. Referring to FIGS. 2A, 2B, and 2C, the structure of the cell culture chamber according to Embodiment 2 of the present invention is described. FIG. 2A is a plan view showing the structure of the cell culture chamber according to Embodiment 2. FIG. 2B is a plan view showing an enlarged structure inside the dashed line shown in FIG. 2A. FIG. 2C is a cross-sectional diagram taken along the line IIC-IIC' of FIG. 2B.

As shown in FIG. 2A, the cell culture chamber has irregular patterns forming a plurality of micro-space structures. As shown in FIG. 2C, the irregular patters are each formed as a two-stage step. In other words, on the surface on which the cells of the cell culture chamber are cultured, there are formed two-stage protrusions 5 that include first protrusions 3 formed in a lattice form, and second protrusions 4 formed on the first protrusions 3 each having a shape of rectangular parallelepiped. Each recess 2 is a space formed by the two-stage protrusions 5. Specifically, the recess 2 is formed of a recess completely surrounded by the first protrusions 3 and a recess formed by the second protrusions 4. A side wall 6 of each first protrusion 3 and a side wall 7 of each second protrusion 4 are formed substantially vertically with respect to the bottom surface. Further, the microprojections 1 are formed on the bottom surface of the recess 2. Note that the microprojections 1 may be formed on the entire surface on which the cells are cultured or may be formed on a part of the surface.

The first protrusions 3 are formed in a lattice form so as to surround the four sides of each rectangular recess 2 as shown in FIG. 2A. The second protrusions 4 are arranged in an island shape on the first protrusions 3 between the adjacent recesses 2. The second protrusions 4 are formed on the four sides of each rectangular recess 2. Accordingly, the recess 2 is not completely surrounded, and the adjacent recesses 2 are communicate with each other at four vertexes of the rectangular shape. Note that irregular patterns are preferably formed in a step shape with two or more steps, or may be formed in a one-step shape.

In the cell culture chamber which includes a plurality of micro-space structures and which is made of resin, the microprojections 1 satisfying the desired width or diameter and aspect ratio are formed, which allows a wide range of applications such as a controlled test for the growth direction and the form of cells, as well as for the adhesion ability, differentiation/proliferation function of cells. Further, the cell culture chamber has sufficiently high accuracy as compared with the conventional glass plate with patterns. Furthermore, since the cell culture chamber can be fabricated at low cost, the cell culture chamber is particularly suitable for the industrial application in which a large amount of cell culture chambers are used while making the best use of the advantage.

A description is given of a method of manufacturing a cell culture chamber which includes a plurality of micro-space structures on the surface where cells are cultured, and which is made of resin. The manufacturing method includes the steps of: forming micro-space structures above a substrate; depositing a metal in accordance with a pattern of the micro-space structures formed above the substrate, or a transcription pattern thereof to form a metal structure having a reverse pattern of the structural pattern of a resin plate; and transcribing the pattern of the metal structure to form the resin plate.

Details of the method are given below.
(i) Formation of a first resist layer on a substrate
(ii) Alignment between the substrate and a mask A
(iii) Exposure of the first resist layer using the mask A
(iv) Heat treatment of the first resist layer
(v) Formation of a second resist layer on the first resist layer
(vi) Alignment of the substrate and a mask B
(vii) Exposure of the second resist layer using the mask B
(viii) Heat treatment of the second resist layer
(ix) Development of the resist layers The above processes are performed to form a desired resist pattern.
(x) Further, the formed resist pattern is subjected to a conduction process, and a metal structure is then deposited above the substrate by plating in accordance with the formed resist pattern.
(xi) Form a resin molded product with the metal structure being used as a mold.

Thus, the cell culture chamber is manufactured.

The steps (V) to (viii) are optional and can be omitted. Meanwhile, the steps (v) to (viii) can be repeated multiple number of times.

The resist pattern forming process is described in more detail.

In the case of obtaining a structure having a depth of 30 µm and a structure having a depth of 100 µm on the substrate, for example, the first resist layer (having a thickness of 70 µm) and the second resist layer (having a thickness of 30 µm) are formed in the stated order, and the exposure or the exposure and heat treatment is carried out on each of the layers. In the development step, a pattern having a depth of 30 µm and serving as the second resist layer is first obtained, and a pattern having a combined depth of 100 µm of the first resist layer and the second resist layer is then obtained. At the time when the pattern having the depth of 100 µm is obtained, in order to prevent the pattern, which has the depth of 30 µm and serves as the second resist layer, from being dissolved or distorted in developer, it is necessary to control the solubility of each layer in the developer.

One method of developing the alkali resistance of photodegradable positive resist is to increase a baking time (solvent drying time) so as to harden the resist. The baking time of the resist is normally adjusted according to the thickness of a layer, the concentration of a solvent such as thinner, and the sensitivity. Increasing the baking time can develop the alkali resistance. Overbaking of the first resist layer hardens the resist too much, which makes it difficult to dissolve a part irradiated with light and form a pattern in the subsequent development step. Thus, it is preferable to select baking conditions by reducing the baking time and so on. Equipment used for the baking is not particularly limited as long as it can dry a solvent. An oven, a hot plate, a hot-air dryer, and the like can be employed. Since the development of the alkali resistance of the photodegradable positive resist is limited compared to a photocrosslinkable negative resist, the photodegradable positive resist, the combined thickness of each resist layer is preferably in a range of 5 to 200 µm, and more preferably, in a range of 10 to 100 µm.

Besides the optimization of the baking time, another method of developing the alkali resistance of the photocrosslinkable negative resist is optimization of crosslink density. In general, the crosslink density of the negative resist can be set according to the exposure amount. In the case of chemical amplification resist, the crosslink density can be set according to the exposure amount and the heat treatment time. The alkali resistance can be developed by increasing the exposure amount or the heat treatment time. In the case of the photocrosslinkable negative resist, the combined thickness of each resist layer is preferably set in a range of 5 to 500 µm, and more preferably, in a range of 10 to 300 µm.

(i) The formation of a first resist layer 12 on a substrate 11 is described below.

Figure 3A:
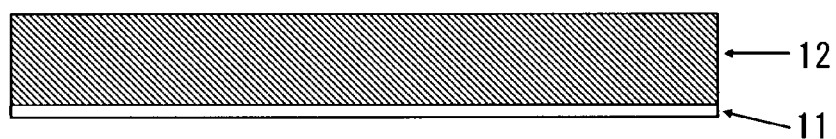
FIG. 3A is a diagram schematically showing a method of producing the cell culture chamber according to Embodiment 2 of the present invention.

FIG. 3A shows a state where the first resist layer 12 is formed on the substrate 11. The flatness of a cell chamber, which is made of resin and obtained by the molded product formation step, is determined by the step of forming the first resist layer 12 on the substrate 11. Thus, the flatness obtained when the first resist layer 12 is formed on the substrate 11 is reflected in the flatness of the metal structure and the cell culture chamber eventually.

Though a method of forming the first resist layer 12 on the substrate 11 is not limited in any way, spin coating, dip coating, roll coating, dry film resist lamination, and the like are generally used. In particular, the spin coating is a method of applying resist onto a spinning glass substrate, which is advantageous in very flat coating of resist on a glass substrate with a diameter of more than 300 mm. The spin coating is thus preferred for use to achieve high flatness.

Both positive resist and negative resist may be used for resist as the first resist layer 12. In either case, the depth of focus on the resist changes depending on the resist sensitivity and exposure conditions. Accordingly, when a UV exposure system is used, for example, it is preferable to select an exposure time and a UV output level according to the type, thickness, and sensitivity of the resist.

If the resist used as the first resist layer 12 is wet resist, as a method of obtaining a given resist thickness by the spin coating, for example, a method of changing the spin coating rotation speed or a method of adjusting the viscosity may be used. The method of changing the spin coating rotation speed is used for obtaining a given resist thickness by appropriately setting the rotation speed of a spin coater. The method of adjusting the viscosity is used for adjusting the resist viscosity according to the flatness required for practical use, since there is a fear that the degradation of flatness may occur if the resist is thick or an resist coated area is large.

In the spin coating, for example, the thickness of the resist layer coated at a time is preferably in a range of 10 to 50 µm, and more preferably, 20 to 50 µm, to maintain high flatness. In order to obtain a given resist layer thickness while retaining high flatness, the resist layer can be formed a plurality of number of times.

When the positive resist is used for the first resist layer 12, if a baking time (solvent drying) is extremely long, the resist is excessively hardened, which makes it difficult to form a pattern in the subsequent development step. Thus, it is preferable to appropriately select baking conditions by reducing the baking time and so on if the resist thickness is set to be smaller than 100 µm.

(ii) The alignment between the substrate 11 and a mask A 13 is described below.

To satisfy a given positional relationship between the pattern of the first resist layer 12 and the pattern of a second resist layer 14 according to a desired design, accurate alignment is necessary at the time of exposure using the mask A 13. Alignment methods include a method of carrying out a cutting operation on the corresponding positions of the substrate 11 and the mask A 13 and fixing them with pins, a method of alignment the positions by laser interferometry, and a method of creating position marks in the corresponding positions of the substrate 11 and the mask A 13 and performing alignment using an optical microscope. In the method of performing alignment using an optical microscope, a position mark is created on the substrate 11 by photolithography technique and a position mark is created on the mask A 13 by laser beam equipment, for example. This method is effective in that the accuracy within 5 μm can be easily obtained by manual operation using the optical microscope.

(iii) The exposure of the first resist layer 12 with the mask A 13 is described below.

Figure 3B:
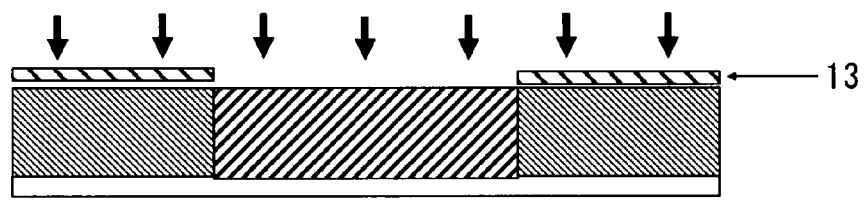
FIG. 3B is a diagram schematically showing the method of producing the cell culture chamber according to Embodiment 2 of the present invention.

The mask A 13 used in the step shown in FIG. 3B is not limited in any way. An emulsion mask, a chromium mask, and the like can be used. In the resist pattern formation step, the size and the accuracy depend on the mask A 13 used. The size and the accuracy are reflected in the cell culture chamber made of resin. Accordingly, to obtain a cell culture chamber made of resin and having a given size and accuracy, it is necessary to specify the size and the accuracy of the mask A 13. A method of increasing the accuracy of the mask A 13 is not limited in any way. For example, there can be employed a method of replacing a laser light source used for the pattern formation of the mask A 13 with one having a shorter wavelength. This method, however, requires high facility costs, which results in higher fabrication costs of the mask A 13. It is thus preferable to appropriately specify the mask accuracy according to the accuracy required for practical use of the cell culture chamber made of resin.

The material of the mask A 13 is preferably quartz glass in terms of temperature expansion coefficient, UV light transmission and absorption characteristics. However, since quartz glass is comparatively expensive, it is thus preferable to appropriately specify the material of the mask A 13 according to the accuracy required for practical use of the resin molded product. In order to obtain a desired structure with different depths or heights or a structure in which the first resist pattern and the second resist pattern are different from each other, as designed, it is necessary to ensure the design of the patterns (transmitting/shielding parts) of the masks used for the exposure of the first resist layer 12 and the second resist layer 14. An approach to achieve this is to perform simulation using CAE analysis software.

The light source used for the exposure is preferably ultraviolet light or laser light for low facility costs. Though synchrotron radiation may be used to make deep exposure, it requires high facility costs and thus substantially increases the price of the resin plate.

Since exposure conditions such as exposure time and intensity vary depending on the material, thickness, and the like of the first resist layer 12, the exposure conditions are preferably adjusted according to the pattern to be formed. The adjustment of the exposure conditions is important since the exposure conditions affect particularly the size and the accuracy of a space structure pattern. Further, since the depth of focus changes depending on the resist type, when the UV exposure system is used, for example, it is preferable to appropriately select an exposure time and a UV output level according to the thickness and sensitivity of the resist.

(iv) The heat treatment of the first resist layer 12 is described below.

Heat treatment called annealing is known as the heat treatment after the exposure to correct the shape of the resist pattern. Here, the heat treatment aims at chemical crosslinking and is carried out only when chemical amplification negative resist is used. The chemical amplification negative resist is mainly formed of a two- or three-component system. For example, the terminal epoxy group of a chemical structure is ring-opened by exposure light and crosslinking reaction is carried out by the heat treatment. When the film thickness is 100 μm, for example, the crosslinking reaction progresses in the heat treatment time of several minutes at the set temperature of 100° C.

Excessive heat treatment of the first resist layer 12 makes it difficult to dissolve a non-crosslinked part to form a pattern in the subsequent development step. Thus, if the resist thickness is set to be smaller than 100 μm, it is preferable to appropriately select the operation by reducing the heat treatment time, carrying out the heat treatment only on the second resist layer 14 formed later, and so on.

(v) The formation of the second resist layer 14 on the first resist layer 12 is described below.

Figure 3C:
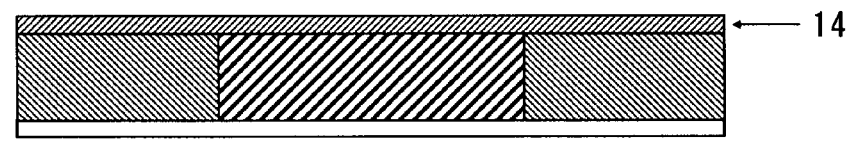
FIG. 3C is a diagram schematically showing the method of producing the cell culture chamber according to Embodiment 2 of the present invention.

FIG. 3C shows a state where the second resist layer 14 is formed. The second resist layer 14 may be formed by the same method as the formation of the first resist layer 12 described in the above item (i). In the case of forming a resist layer using positive resist by the spin coating, increasing the baking time about 1.5 to 2 times longer than usual enables development of the alkali resistance. It is thereby possible to prevent the dissolution or distortion of the resist pattern of the second resist layer 14 at the completion of the development of the first resist layer 12 and the second resist layer 14.

(vi) The alignment between the substrate 11 and a mask B 15 is described below.

The alignment between the substrate 11 and the mask B 15 is performed in the same manner as the alignment between the substrate 11 and the mask A 13 described in the above item (ii).

(vii) The exposure of the second resist layer 14 with the mask B 15 is described below.

Figure 3D:
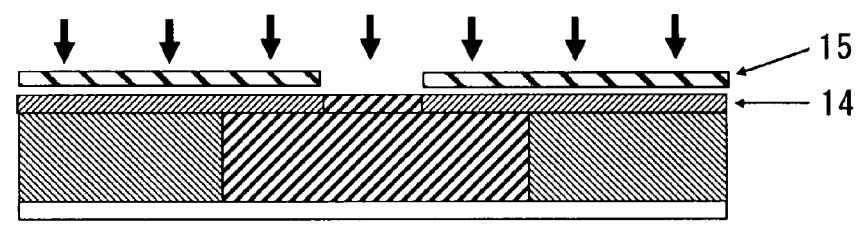
FIG. 3D is a diagram schematically showing the method of producing the cell culture chamber according to Embodiment 2 of the present invention.

The exposure of the second resist layer 14 with the mask B 15 is performed in the same manner as the exposure of the first resist layer 12 with the mask A 13 described in the above item (iii). FIG. 3D shows a state where the second resist layer 14 is subjected to exposure.

(viii) The heat treatment of the second resist layer 14 is described below.

The heat treatment of the second resist layer 14 is performed by the same method as the heat treatment of the first resist layer 12 described in the above item (iv). The heat treatment of the second resist layer 14 is performed in order to avoid the dissolution or distortion of the pattern of the second resist layer 14 when the pattern of the first resist layer 12 is obtained in the subsequent development step. The heat treatment enhances the chemical crosslinking to increase the crosslink density, thereby developing the alkali resistance. The heat treatment time for developing the alkali resistance is preferably selected according to the resist thickness from a range of 1.1 to 2.0 times longer than usual.

(ix) The development of the resist layers 12 and 14 is described below.

Figure 3E:
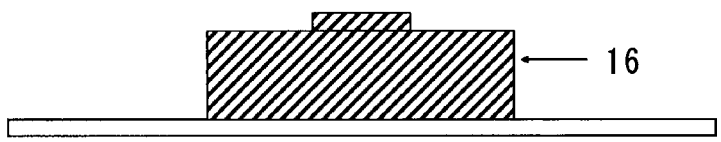
FIG. 3E is a diagram schematically showing the method of producing the cell culture chamber according to Embodiment 2 of the present invention.

In the development step shown in FIG. 3E, it is preferable to use a given developer suitable for the resist used. It is preferable to adjust development conditions such as development time, development temperature, and developer concentration according to the resist thickness and pattern shape.

Setting appropriate conditions is preferred since overlong development time to obtain the required depth causes the pattern to be larger than a given size, for example. By the development process, a resist pattern 16 is formed.

Examples of methods to increase the flatness accuracy of the top surface of the cell culture chamber or the bottom of the micropattern include a method of changing the type of resist (negative or positive) used in the resist coating and a method of polishing the surface of a metal structure.

Note that, in the case of forming a plurality of resist layers to obtain a desired mold depth, it is possible to perform the exposure and development of the plurality of resist layers at the same time. Alternatively, it is possible to form and expose one resist layer and further form and expose another resist layer, and then perform the development of the two resist layers at the same time.

(x) The metal structure formation step is described in more detail.

The metal structure formation step is a step of depositing a metal over the resist pattern 16 obtained by the resist pattern formation step to form the micro-space structure surface of a metal structure 18 in accordance with the resist pattern 16, thereby obtaining the metal structure 18.

Figure 3F:
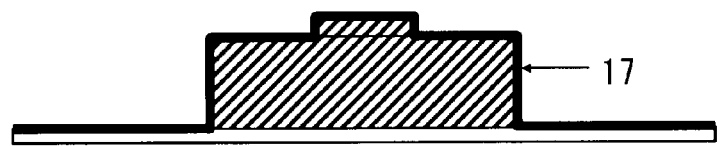
FIG. 3F is a diagram schematically showing the method of producing the cell culture chamber according to Embodiment 2 of the present invention.

As shown in FIG. 3F, in this step, a conductive layer 17 is formed in advance in accordance with the resist pattern 16. Though a method of forming the conductive layer 17 is not particularly limited, it is preferable to use vacuum evaporation, sputtering, and the like. Examples of the conductive material used for the conductive layer 17 include gold, silver, platinum, copper, and aluminum.

Figure 3G:
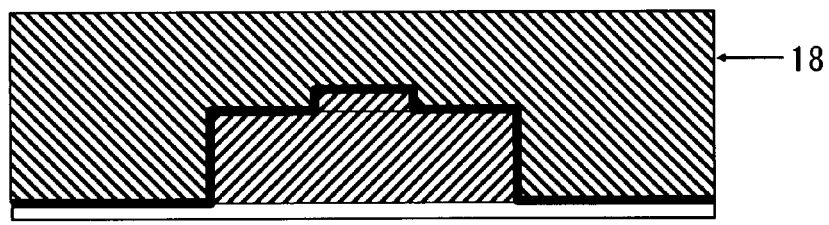
FIG. 3G is a diagram schematically showing the method of producing the cell culture chamber according to Embodiment 2 of the present invention.

As shown in FIG. 3G, after the formation of the conductive film 17, a metal is deposited by plating in accordance with the resist pattern 16, thereby forming the metal structure 18. The plating method is not particularly limited. For example, electrolytic plating and electroless plating can be employed. Metals to be used are not particularly limited. Nickel, nickel and cobalt alloy, copper, or gold may be used, for example. Nickel is preferred since it is less costly and durable.

The metal structure 18 may be polished depending on its surface condition. In this case, to prevent contaminations from attaching to a shaped article, it is preferable to perform ultrasonic cleaning after the polishing. Further, it is also possible to perform surface treatment of the metal structure 18 with mold release agent and the like so as to improve the surface condition. Note that an angle of gradient along a depth direction of the metal structure 18 is preferably 50° to 90°, and more preferably, 60° to 87° for the shape of the resin molded product. The metal structure 18 deposited by plating is separated from the resist pattern 16.

(xi) The molded product formation step is described in more detail.

Figure 3H:
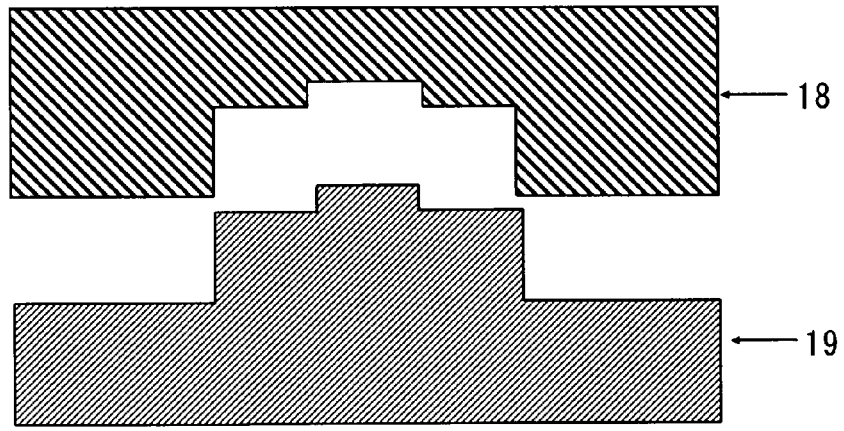
FIG. 3H is a diagram schematically showing the method of producing the cell culture chamber according to Embodiment 2 of the present invention.

The molded product formation step is a step of forming a resin molded product 19 by using the metal structure 18 as a mold as shown in FIG. 3H. Though a method of forming the resin molded product 19 is not particularly limited, injection molding, press molding, monomer casting, solvent casting, or a roll transfer method using extrusion molding may be used, for example. The injection molding is preferred for its high productivity and transcription property. If the resin molded product 19 is formed by the injection molding using the metal structure 18 with a given size as a mold, it is possible to reproduce the shape of the metal structure 18 to the resin molded product 19 with a high transcription rate. The transcription rate may be determined by using an optical microscope, a scanning electron microscope (SEM), a transmission electron microscope (TEM), and the like.

The minimum value of the flatness of the resin molded product 19 is preferably 1 µm or larger to enable easy industrial reproduction. The maximum value of the flatness of the resin molded product 19 is preferably 200 µm or smaller in order not to cause a problem, for example, in contact of the molded product to an optical system unit due to a warp or the like. The dimensional accuracy of a shaped part of the resin molded product is preferably within a range of ±0.5 to 10% to enable easy industrial reproduction.

Hereinafter, examples and comparative examples of the present invention are described. In those examples and comparative examples, the dimensions and aspect ratio of microprojections are varied, and an adhesion ability and a differentiation/proliferation ability of cultured cells were analyzed. The dimensions and aspect ratio of the microprojections were measured by a stylus method using a surface profile measuring system (DEKTAK 3030) manufactured by ULVAC, Inc. Optical properties of a whole light transmittance and a haze value were measured using a visible light transmittance meter (type: HA-TR) manufactured by SUGA TEST instruments CO., LTD. Specifically, the whole light transmittance was measured twice by a method compliant with JIS K6714, thereby obtaining the average value. Further, the adhesion ability of cells was analyzed by crystal violet method known as calorimetric analysis. The differentiation/proliferation ability of cells was analyzed by MTT method known as colorimetric analysis, while Comparative Example 1 was regarded as 100%.

The crystal violet method is calorimetric analysis utilizing the fact that crystal violet is incorporated into living cells. Specifically, $5.0 \times 10^5$ HeLa cells were cultured in an incubator for 2 hours, and the cells were then washed with normal saline, thereby distinguishing cells adhered to the substrate from floating (dead) cells. Next, the cells were stained with crystal violet, and the cells adhered to the substrate were then dissolved using sodium dodecyl sulfate (SDS) solution, thereby measuring the absorbance at a wavelength of 540 nm to be compared with Comparative Example 1.

The MTT method is a staining method utilizing the fact that MTT (a kind of tetrazolium salt) is converted into formazan by a reaction of dehydrogenase in the cells. Active cells show a high enzymatic activity, a high reduction to formazan, and a high formazan concentration. A difference in concentration is utilized as an absorbance in cell counting. Specifically, $5.0 \times 10^5$ HeLa cells were cultured in the incubator for three hours, and the cells were then washed with normal saline, thereby distinguishing cells adhered to the substrate from floating (dead) cells. The cells were cultured in the incubator for 48 hours, and then the solution was replaced with culture solution containing MTT and the cell culture was further continued for three hours. Then, isopropanol was added to dissolve the formazan, and the absorbance at a wavelength of 570 nm was measured to be compared with Comparative Example 1.

COMPARATIVE EXAMPLE 1

A commercially-available sterilized petri dish (90 mm in diameter and 20 mm in depth) made of polystyrene was used. The shape of projections formed on the surface on which the cells are cultured has a width of 10 nm and an aspect ratio of 0.05. As optical properties, a whole light transmittance of 87% and a haze value of 2.0% were obtained.

COMPARATIVE EXAMPLE 2

By using an acrylic resin (parapet GH-S) produced by KURARAY CO., LTD., a resin plate having a width of 24 mm, a length of 74 mm, and a thickness of 1.0 mm was produced by injection molding, and the resin plate was then sterilized. A mold mirror surface, which contacts the surface of the resin plate, was subjected to mirror finish so as to conform to optical media. The shape of projections formed on the surface on which cells are cultured has a width of 7 nm and an aspect ratio of 0.1. As optical properties, a whole light transmittance of 91% and a haze value of 2.1% were obtained.

COMPARATIVE EXAMPLE 3

By using an acrylic resin (parapet GH-S) produced by KURARAY CO., LTD., a resin plate having a width of 24 mm, a length of 74 mm, and a thickness of 1.0 mm was produced by injection molding, and the resin plate was then sterilized. As a mold mirror surface, which contacts the surface of the resin plate, one for general-purpose resin was used. The shape of projections formed on the surface on which cells are cultured has a width of 15 nm and an aspect ratio of 0.1. As optical properties, a whole light transmittance of 90% and a haze value of 2.8% were obtained.

COMPARATIVE EXAMPLE 4

By using an acrylic resin (parapet GH-S) produced by KURARAY CO., LTD., a resin plate having a width of 24 mm, a length of 74 mm, and a thickness of 1.0 mm was produced by injection molding, and the resin plate was then sterilized. To a mold, which contacts the surface of the resin plate, a stamper having a width of 5.5 μm and an aspect ratio of 5 was formed and fixed. The shape of projections formed on the surface on which cells are cultured has a width of 5 μm and an aspect ratio of 4.5. As optical properties, a whole light transmittance of 72% and a haze value of 25.6% were obtained.

EXAMPLE 1

By using an acrylic resin (parapet GH-S) produced by KURARAY CO., LTD., a resin plate having a width of 24 mm, a length of 74 mm, and a thickness of 1.0 mm was produced by injection molding, and the resin plate was then sterilized. As a mold mirror surface, which contacts the surface of the resin plate, one for general-purpose resin was used. Then, sandblasting was carried out on the resin plate to form microprojections on the surface on which cells were to be cultured. The shape of the projections formed on the surface on which cells are cultured has a width of 2.5 μm and an aspect ratio of 2.0. As optical properties, a whole light transmittance of 76% and a haze value of 17.3% were obtained.

EXAMPLE 2

By using an acrylic resin (parapet GH-S) produced by KURARAY CO., LTD., a resin plate having a width of 24 mm, a length of 74 mm, and a thickness of 1.0 mm was produced by injection molding, and the resin plate was then sterilized. As a mold mirror surface, which contacts the surface of the resin plate, one for general-purpose resin was used. Then, sandblasting was carried out on the resin plate to form microprojections on the surface on which cells were to be cultured. Then, an inorganic film was deposited on the microprojections by vacuum evaporation using an evaporation system (type: UEP) manufactured by ULVAC, Inc. As a material of a target used for the evaporation, $SiO_2$ with a film thickness of 0.5 μm was used. The shape of the projections formed on the surface on which cells are cultured has a width of 800 nm and an aspect ratio of 1.0. As optical properties, a whole light transmittance of 78% and a haze value of 13.8% were obtained.

EXAMPLE 3

By using an acrylic resin (parapet GH-S) produced by KURARAY CO., LTD., a resin plate having a width of 24 mm, a length of 74 mm, and a thickness of 1.0 mm was produced by injection molding, and the resin plate was then sterilized. As a mold mirror surface, which contacts the surface of the resin plate, one for general-purpose resin was used. Then, microprojections were formed by vacuum evaporation using an evaporation system (type: UEP) manufactured by ULVAC, Inc. As a material of a target used for the evaporation, $SiO_2$ with a film thickness of 0.2 μm was used. The shape of the projections formed on the surface on which cells are cultured has a width of 280 nm and an aspect ratio of 1.0. As optical properties, a whole light transmittance of 88% and a haze value of 3.0% were obtained.

EXAMPLE 4

By using an acrylic resin (parapet GH-S) produced by KURARAY CO., LTD., a resin plate having a width of 24 mm, a length of 74 mm, and a thickness of 1.0 mm was produced by injection molding, and the resin plate was then sterilized. As a mold mirror surface, which contacts the surface of the resin plate, one for general-purpose resin was used. Then, microprojections were formed by vacuum evaporation using an evaporation system (type: UEP) manufactured by ULVAC, Inc. As a material of a target used for the evaporation, $SiO_2$ with a film thickness of 0.1 μm was used. The shape of the projections formed on the surface on which cells are cultured has a width of 150 nm and an aspect ratio of 0.8. As optical properties, a whole light transmittance of 90% and a haze value of 2.5% were obtained.

EXAMPLE 5

Figure 4:
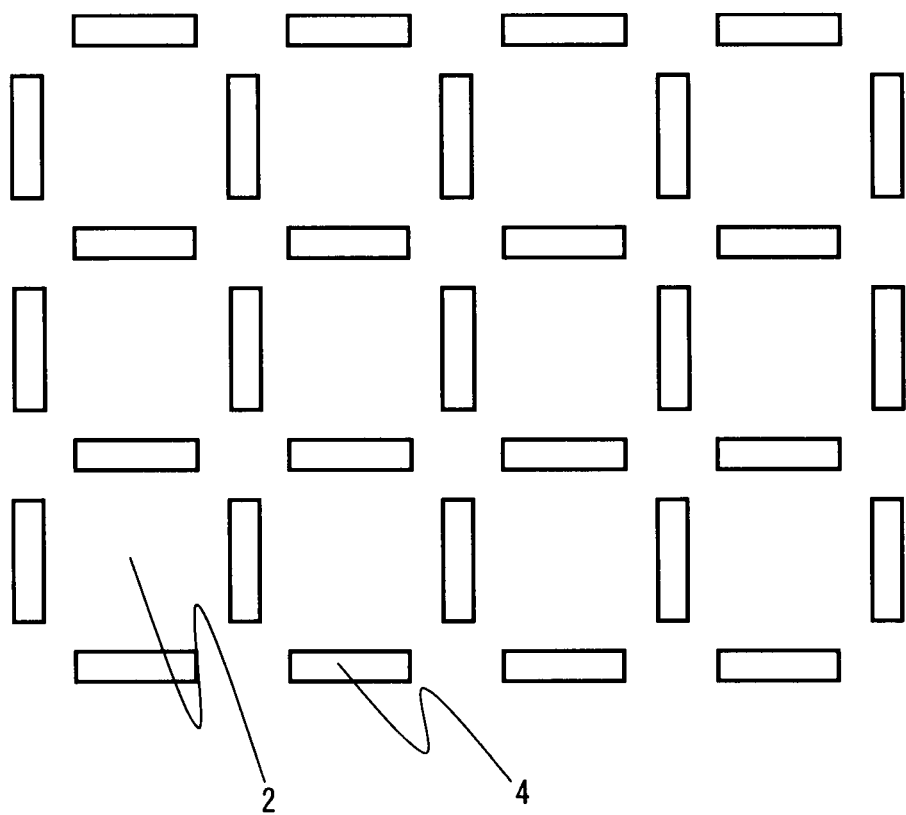
FIG. 4 is a plan view schematically showing a cell culture chamber according to Example 5 of the present invention.

By using an acrylic resin (parapet GH-S) produced by KURARAY CO., LTD., a plate having micro-space structures formed of a plurality of side walls each having a height of 20 μm was formed on a resin plate having a width of 24 mm, a length of 74 mm, and a thickness of 1.0 mm by injection molding using a stamper. FIG. 4 is a plan view showing the structure of the cell culture chamber according to Example 5 of the present invention. The structure does not include the first projections 3 shown in FIG. 2 but includes second projections 4. The second projections 4 has dimensions of 10 μm in width, 60 μm in length, 20 μm in height, and has an arrangement pitch of 100 μm in both the longitudinal and lateral directions. As a mold mirror surface, which contacts the surface of the resin plate, one for general-purpose resin was used. The resin plate was sterilized, and microprojections were then formed by vacuum evaporation using an evaporation system (type: UEP) manufactured by ULVAC, Inc. As a material of a target used for the evaporation, $SiO_2$ with a film thickness of 0.3 μm was used. The shape of the projections formed on the surface on which cells were cultured has a width of 180 nm and an aspect ratio of 0.6. As optical properties, a whole light transmittance of 89% and a haze value of 6.6% were obtained.

The results of the comparative examples and examples are shown in Table 1.

TABLE 1

| | Shape of projections | | Optical properties (%) | | | Differentiation/ |
|---|---|---|---|---|---|---|
| | Width (Diameter) | Aspect ratio | Trans-mittance | Haze value | Adhesion ability (%) | proliferation ability (%) |
| Comparative Example 1 | 10 nm | 0.05 | 87 | 2.0 | 100 | 100 |
| Comparative Example 2 | 7 nm | 0.1 | 91 | 2.1 | 65 | 40 |
| Comparative Example 3 | 15 nm | 0.1 | 90 | 2.8 | 97 | 94 |
| Comparative Example 4 | 5 μm | 4.5 | 72 | 25.6 | 80 | 75 |
| Example 1 | 2.5 μm | 2.0 | 76 | 17.3 | 145 | 150 |
| Example 2 | 800 nm | 1.0 | 78 | 13.8 | 180 | 170 |
| Example 3 | 280 nm | 1.0 | 88 | 3.0 | 140 | 135 |
| Example 4 | 150 nm | 0.8 | 90 | 2.5 | 130 | 160 |
| Example 5 | 180 nm | 0.6 | 89 | 6.6 | 160 | 180 |

In comparison with Comparative Example 1, when the width of the projections formed on the surface on which cells are cultured is smaller than 20 nm or larger than 3 μm, the adhesion ability of the cells is reduced or less effective. When the aspect ratio is smaller than 0.2 or larger than 3.0, the adhesion ability of the cells is also reduced or less effective. When the width and the aspect ratio of the projections are increased, the transparency is also reduced.

The examples show the adhesion ability extremely higher than that of Comparative Example 1 when the projection width is set in a range of 20 nm to 30 μm and when the aspect ratio is set in a range of 0.2 to 3.0. The HeLa cells used in this test show the highest adhesion ability when the projection width is 800 nm. Since cells are different in size and activity, the optimum value for each type of cells may vary. However, when the desired range is reached, excellent adhesion performance can be expected.

Example 3 to 5 show that, when the projection width is set to be equal to or smaller than 400 nm, both the high transparency and the cell adhesion are achieved. This indicates the high applicability in the use for observing cells with transmitted light.

In comparison with Comparative Example 1, when the width of the projections formed on the surface on which cells are cultured is smaller than 20 nm or larger than 3 μm, the differentiation/proliferation ability of the cells is reduced or less effective. When the aspect ratio is smaller than 0.2 or larger than 3.0, the differentiation/proliferation ability of the cells is also reduced or less effective. When the projection width and the aspect ratio are increased, the transparency is also reduced.

The examples show the differentiation/proliferation ability of the cells extremely higher than that of Comparative Example 1 when the projection width is set in a range of 20 nm to 3 μm and when the aspect ratio is set in a range of 0.2 to 3.0. The HeLa cells used in this test show the highest differentiation/proliferation ability of the cells when the projection width is 800 nm. Since cells are different in size and activity, the optimum value for each type of cells may vary. However, when the desired range is reached, the excellent differentiation/proliferation ability of cells can be expected.

Examples 3 to 5 show that, when the projection width is set to be equal to or smaller than 400 nm, both the high transparency and the differentiation/proliferation ability of cells are achieved. This indicates the high applicability in the use for observing cells with transmitted light. Especially in Example 5, the result of a culture test for pheochromocytoma (PC12) showed that cultured cells formed a network each other.

Industrial Applicability

The present invention is applied to a cell culture chamber in use for, for example, culture, test, and inspection of cells isolated from tissue.

The invention claimed is:

1. A cell culture chamber including a mass of projections formed of a plurality of microprojections on a surface on which cells are cultured,
    wherein a width or diameter of each of the microprojections is in a range of 20 nm to 3 μm, and wherein each of the microprojections has a height of 4 nm to 3 μm, and
    wherein the surface on which the cells are cultured has a plurality of micro-space structures having a height of 10 μm to 500 μm,
    wherein the plurality of micro-space structures surround the plurality of microprojections.

2. The cell culture chamber according to claim 1, wherein the width or diameter of each of the microprojections is in a range of 20 nm to 400 nm.

3. The cell culture chamber according to claim 1, wherein a whole or a part of the cell culture chamber is coated with an organic film or an inorganic film.

4. The cell culture chamber according to claim 2, wherein a whole or a part of the cell culture chamber is coated with an organic film or an inorganic film.

5. The cell culture chamber according to claim 2, wherein the surface on which the cells are cultured has a plurality of micro-space structures.

6. The cell culture chamber according to claim 3, wherein the surface on which the cells are cultured has a plurality of micro-space structures.

7. The cell culture chamber according to claim 4, wherein the surface on which the cells are cultured has a plurality of micro-space structures.

8. The cell culture chamber according to claim 1, wherein the plurality of micro-space structures have a height of 10 μm to 300 μm.

* * * * *

UNITED STATES PATENT AND TRADEMARK OFFICE
CERTIFICATE OF CORRECTION

PATENT NO. : 8,435,782 B2  Page 1 of 1
APPLICATION NO. : 12/280607
DATED : May 7, 2013
INVENTOR(S) : Nishi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 530 days.

Signed and Sealed this
Eighth Day of September, 2015

Michelle K. Lee
*Director of the United States Patent and Trademark Office*